US010390915B2

(12) United States Patent
Moskovich et al.

(10) Patent No.: US 10,390,915 B2
(45) Date of Patent: Aug. 27, 2019

(54) ORAL CARE IMPLEMENT WITH APPLICATOR

(71) Applicant: COLGATE-PALMOLIVE COMPANY, New York, NY (US)

(72) Inventors: Robert Moskovich, East Brunswick, NJ (US); Kelly Gail Duncan, Washington, NJ (US); Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 239 days.

(21) Appl. No.: 15/106,370

(22) PCT Filed: Dec. 18, 2013

(86) PCT No.: PCT/US2013/076117
§ 371 (c)(1),
(2) Date: Jun. 20, 2016

(87) PCT Pub. No.: WO2015/094225
PCT Pub. Date: Jun. 25, 2015

(65) Prior Publication Data
US 2016/0331496 A1    Nov. 17, 2016

(51) Int. Cl.
*A46B 9/04*     (2006.01)
*A46B 11/00*    (2006.01)
(Continued)

(52) U.S. Cl.
CPC ............ *A61C 17/0211* (2013.01); *A46B 9/04* (2013.01); *A46B 11/0055* (2013.01);
(Continued)

(58) Field of Classification Search
CPC ............ A61C 17/0211; A61C 17/0202; A61C 17/227; A61C 17/225; A61C 17/0214;
(Continued)

(56) References Cited

U.S. PATENT DOCUMENTS 3,391,696 A * 7/1968 Woodward ......... A61C 17/0202
433/89
3,738,762 A   6/1973 Moore
(Continued)

FOREIGN PATENT DOCUMENTS

WO    WO2007046114    4/2007

OTHER PUBLICATIONS

Corresponding International Search Report for PCT/US2013/076117 dated Sep. 4, 2014.

*Primary Examiner* — Wade Miles
*Assistant Examiner* — Drew S Folgmann

(57) ABSTRACT

An oral care implement having an applicator. In one aspect, the invention can be an oral care implement having: a body having a handle and a head coupled to a distal end of the handle, the body extending along a longitudinal axis; a store of oral care material located within the body; an applicator on the body, the applicator having a plurality of outlets in fluid communication with the store of oral care material, the plurality of outlets located on a concave dispensing surface of the applicator; and an actuator operably coupled to the store of oral care material to dispense the oral care material through the plurality of outlets.

20 Claims, 6 Drawing Sheets

(51) Int. Cl.
*A61C 17/02* (2006.01)
*A61C 17/22* (2006.01)

(52) U.S. Cl.
CPC ........ *A61C 17/0202* (2013.01); *A61C 17/227* (2013.01); *A46B 2200/1066* (2013.01)

(58) Field of Classification Search
CPC ........... A61C 17/28; A61C 17/36; A46B 9/04; A61H 13/00; A61H 13/005
See application file for complete search history.

(56) References Cited

U.S. PATENT DOCUMENTS

| | | | | |
|---|---|---|---|---|
| 4,863,380 | A * | 9/1989 | Creed | A61C 17/0202 |
| | | | | 132/322 |
| 5,439,014 | A | 8/1995 | Moussa | |
| 2008/0209650 | A1 * | 9/2008 | Brewer | A46B 15/0002 |
| | | | | 15/22.1 |
| 2009/0208898 | A1 | 8/2009 | Kaplan | |
| 2013/0205524 | A1 * | 8/2013 | Dhami | A46B 5/0095 |
| | | | | 15/104.94 |
| 2014/0259474 | A1 * | 9/2014 | Sokol | A61C 17/3445 |
| | | | | 15/22.2 |
| 2014/0349246 | A1 * | 11/2014 | Johnson | A61C 17/02 |
| | | | | 433/80 |
| 2014/0373290 | A1 * | 12/2014 | Leveling | A61C 17/228 |
| | | | | 15/21.1 |

* cited by examiner

ORAL CARE IMPLEMENT WITH APPLICATOR

BACKGROUND

Oral care implements such as toothbrushes are typically used by applying toothpaste or dentifrice to a bristle section on the head of the toothbrush, followed by brushing regions of the oral cavity (e.g., the teeth or soft tissue such as the tongue and/or gums) with the bristle section. Some toothbrushes have been equipped with internal reservoirs and systems for delivering dentifrice or other oral care materials to a user's oral cavity. In such toothbrushes, an applicator may be used to dispense the dentifrice or other oral care material to the user's oral cavity. Such applicators are typically only capable of dispensing the dentifrice or other oral care material to a single tooth at a time. Using these conventional applicators, it can be an extremely time consuming process to apply the dentifrice or other oral care material to all of a user's teeth. Thus, a need exists for a toothbrush or other oral care implement that can dispense an oral care material to many or all of a user's teeth simultaneously.

BRIEF SUMMARY

Exemplary embodiments according to the present disclosure are directed to an oral care implement having an applicator. In some embodiments the applicator is a spray applicator. The applicator may include a plurality of outlets that are located on a concave dispensing surface of the applicator. In one embodiment, the oral care implement may include a head having tooth cleaning elements and a handle having a plurality of outlets arranged in a longitudinally spaced-apart manner.

In one aspect, the invention can be an oral care implement comprising: a body comprising a handle and a head coupled to a distal end of the handle, the body extending along a longitudinal axis; a store of oral care material located within the body; an applicator on the body, the applicator comprising a plurality of outlets in fluid communication with the store of oral care material, the plurality of outlets located on a concave dispensing surface of the applicator; and an actuator operably coupled to the store of oral care material to dispense the oral care material through the plurality of outlets.

In another aspect, the invention can be an oral care implement comprising: a body comprising a handle and a head coupled to a distal end of the handle, the body extending along a longitudinal axis; a plurality of tooth cleaning elements extending from the head; a store of oral care material located within the body; an applicator on the body, the applicator comprising a plurality of outlets in fluid communication with the store of oral care material, the plurality of outlets positioned on the handle in a longitudinally spaced-apart manner; and an actuator operably coupled to the store of oral care material to dispense the oral care material through the plurality of outlets.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
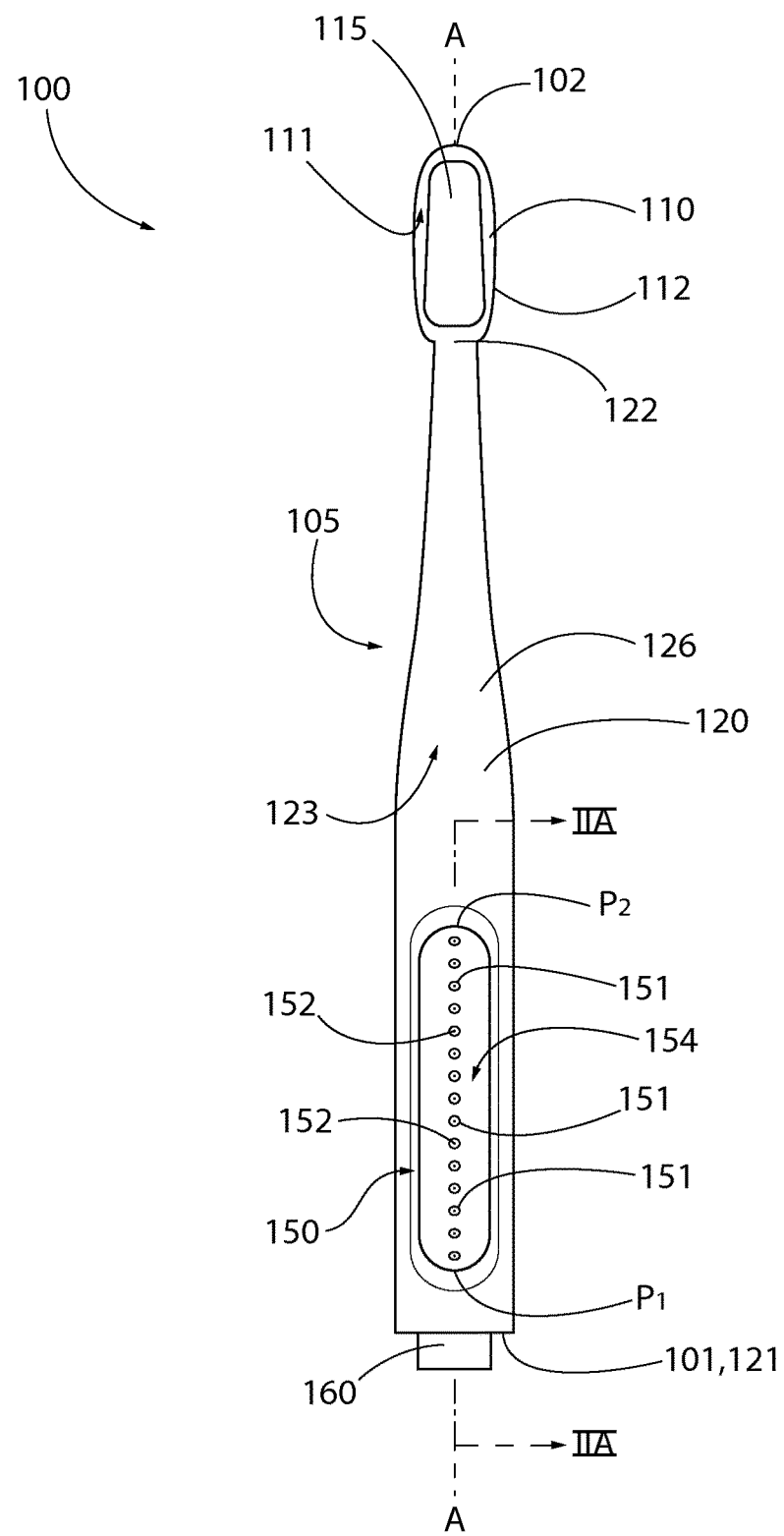
FIG. 1 is a front view of an oral care implement in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring first to FIG. 1, an oral care implement 100 is illustrated in accordance with an embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement 100 generally comprises a body 105 that extends from a proximal end 101 to a distal end 102 along a longitudinal axis A-A. Conceptually, the longitudinal axis A-A is a reference line that is generally coextensive with the three-dimensional center line of the body 105. Because the body 105 may, in certain embodiments, be a non-linear structure, the longitudinal axis A-A of the body 105 may also be non-linear in certain embodiments. However, the invention is not to be so limited in all embodiments and in certain other embodiments the body 105 may have a simple linear arrangement and thus a substantially linear longitudinal axis A-A.

Figure 2A:
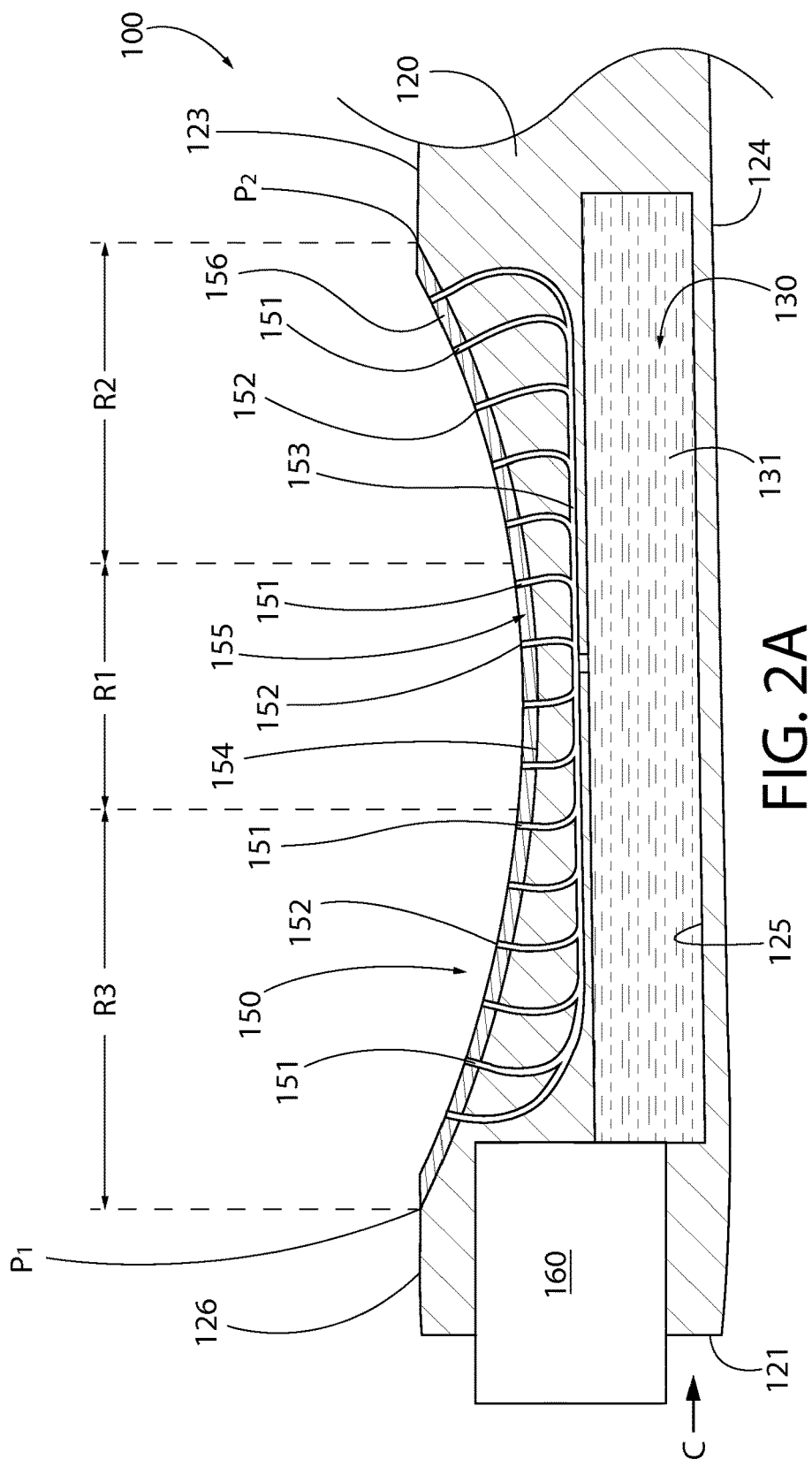
FIG. 2A is a schematic cross-sectional view taken along line IIA-IIA of FIG. 1.

The body 105 of the oral care implement 100 generally comprises a head 110 and a handle 120. The handle 120 is an elongated structure extending from a proximal end 121 (which is also the proximal end 101 of the body 105) to a distal end 122. The handle 120 provides the mechanism by which the user can hold and manipulate the oral care implement 100 during use. The handle 120 comprises a front surface 123 and an opposing rear surface 124 (FIG. 2A). In the exemplified embodiment, the handle 120 is generically depicted having various contours for user comfort. Of course, the invention is not to be so limited in all embodiments and in certain other embodiments the handle 120 can take on a wide variety of shapes, contours and configurations, none of which are limiting of the present invention unless so specified in the claims. In one particular embodiment, the handle 120 has a generally cylindrical shape.

In the exemplified embodiment, the handle 120 is formed of a rigid plastic material, such as for example without limitation polymers and copolymers of ethylene, propylene, butadiene, vinyl compounds and polyesters such as polyethylene terephthalate. In other embodiments the handle 120 can be formed of any material that is not incompatible with an oral care material that is stored therein. Of course, the invention is not to be so limited in all embodiments and the handle 120 may include a resilient material, such as a thermoplastic elastomer, as a grip cover that is molded over portions of or the entirety of the handle 120 to enhance the gripability of the handle 120 during use. For example, portions of the handle 120 that are typically gripped by a user's palm during use may be overmolded with a thermoplastic elastomer or other resilient material to further increase comfort to a user.

The head 110 of the oral care implement 100 is coupled to the handle 120 and comprises a front surface 111 and an opposing rear surface 112. Specifically, the head 110 of the oral care implement 100 is coupled to the distal end 122 of the handle 120. In the exemplified embodiment, the head 110 is formed integrally with the handle 120 as a single unitary structure using a molding, milling, machining or other suitable process. Thus, in such embodiments the body 105 including both the handle 120 and the head 110 is formed from a single shot in an injection molding process or in any other manner known in the art. However, in other embodiments the handle 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Typically, the head 110 is formed of any one of the materials described above for use in forming the handle 120.

In the exemplified embodiment, the head 110 of the oral care implement 100 is provided with a plurality of tooth cleaning elements 115 extending from the front surface 111. In the exemplified embodiment the tooth cleaning elements 115 are generically illustrated. In certain embodiments the exact structure, pattern, orientation and material of the tooth cleaning elements 115 are not to be limiting of the present invention. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 115 of the present invention can be connected to the head 110 in any manner known in the art. For example, staples/anchors, in-mold tufting (IMT) or anchor free tufting (AFT) could be used to mount the cleaning elements/tooth engaging elements to the head 110. In certain embodiments, the invention can be practiced with various combinations of stapled, IMT or AFT bristles. In AFT, a plate or membrane having tuft holes therein is formed separately from the body 105 of the oral care implement 100. Bristles or other tooth cleaning elements are positioned within the tuft holes. The free ends of the bristles on one side of the plate or membrane perform the cleaning function. The ends of the bristles on the other side of the plate or membrane are melted together by heat to be anchored in place. After the bristles are properly coupled to the head plate, the head plate is secured to the brush head such as by ultrasonic welding. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Although not illustrated herein, in certain embodiments the head 110 may also include a soft tissue cleanser coupled to or positioned on its rear surface 112. An example of a suitable soft tissue cleanser that may be used with the present invention and positioned on the rear surface of the head 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

Referring now to FIGS. 1 and 2A concurrently, the oral care implement 100 will be further described. The handle 120 of the oral care implement 100 comprises an inner surface 125 and an outer surface 126. The outer surface 126 of the handle 120 comprises the front and rear surfaces 123, 124 of the handle 120. In the exemplified embodiment, the inner surface 125 of the handle 120 defines a reservoir 130. The reservoir 130 contains a store of oral care material 131 that can be applied to a user's teeth and/or other oral surfaces in order to impart certain oral health benefits to the user's teeth and/or oral cavity. Although the reservoir 130 is described herein as being located within the handle 120, the invention is not to be so limited and in certain other embodiments the reservoir 130 may be formed in any location in the body 105 of the oral care implement 100, including in the head 110 of the oral care implement 100 or in a neck region of the oral care implement 100 that is located between the handle 120 and the head 110. Furthermore, in certain embodiments the reservoir 130 may be omitted and the body 105 may simply contain the store of oral care material 131, which may be provided within a separate housing that is disposed within the body 105 of the oral care implement 100.

The oral care material 131 can be any type of oral care material that is desired to be applied to a user's teeth, gums, or other oral surfaces of the oral cavity to impart a desired benefit to the user's oral cavity. For example, in one embodiment the oral care material may be a mouthwash. In another embodiment the oral care material may be a dentifrice. In yet another embodiment, the oral care material may be a tooth whitening agent, such as peroxide containing tooth whitening compositions. Other contemplated oral care materials include, for example without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

In certain embodiments the oral care material is free of (i.e., is not) toothpaste. Instead, the oral care material in such embodiments is intended to provide benefits in addition to merely brushing one's teeth. Thus, the oral care material may in certain embodiments be used to supplement normal toothbrushing. Other suitable oral care materials could include lip balm or other materials that are typically available in a semi-solid state. Furthermore, in still other embodiments the oral care material can be a natural ingredient, such as for example without limitation, lotus seed; lotus flower, bamboo salt; jasmine; corn mint; camellia; aloe; gingko; tea tree oil; xylitol; sea salt; vitamin C; ginger; cactus; baking soda; pine tree salt; green tea; white pearl; black pearl; charcoal powder; nephrite or jade and Ag/Au+.

The oral care implement 100 further comprises an applicator 150 on the body 105 for dispensing the oral care material 131 to a user's oral cavity. In the exemplified embodiment, the applicator 150 is on the handle 120, and more specifically on the front surface 123 of the handle 120. However, the invention is not to be so limited in all embodiments and the applicator 150 can be located on the head 110 or any other location on the body 105 in other embodiments. Furthermore, although the applicator 150 is illustrated on the front surface 123 of the handle 120 in the exemplified embodiment, in other embodiments the applicator 150 can be on the rear surface 124 of the handle 120 or on a side surface of the handle. In certain embodiments, the applicator 150 is located on the outer surface 126 of the handle 120. The handle 120 can include the entire oral care implement 100 other than the head 110, such that the neck of the oral care implement 100 is considered as a part of the handle 120.

The applicator 150 comprises a plurality of outlets 151, only some of which are labeled in the figures to avoid clutter. Each of the plurality of outlets 151 is in fluid communication with the store of oral care material 131. Thus, the oral care material 131 can be dispensed from the store or reservoir 130, through the outlets 151 and onto a user's teeth or otherwise into a user's oral cavity. In certain embodiments, each of the plurality of outlets 151 is a spray nozzle so that the oral care material 131 can be sprayed through the outlets 151 to distribute and apply the oral care material 131 to a user's oral cavity. In the exemplified embodiment, each of the outlets 151 terminates at an opening 152 formed into the outer surface 126 of the handle 120. Each of the outlets 151 extends from the opening 152 formed into the outer surface 126 of the handle 120 to the reservoir 130, either directly or indirectly via a common manifold 153 as depicted in the exemplified embodiment. Thus, the outlets 151 form a passageway from the store of oral care material 131 to the outer surface 126 of the handle 120.

In the exemplified embodiment, the plurality of outlets 151 are positioned on the handle 120 in a longitudinally spaced-apart manner. Specifically, adjacent outlets 151 are spaced apart from one another in a direction of the longitudinal axis A-A. Furthermore, in the embodiment depicted in FIGS. 1 and 2A, the plurality of outlets 151 are arranged on the handle 120 in a single longitudinal row. More specifically, the plurality of outlets 151 are arranged on the handle 120 in a single row, and the outlets of the single row are longitudinally aligned. Of course, the invention is not to be so limited and multiple rows of outlets can be used in other embodiments, such as the embodiment depicted in FIGS. 6 and 7 discussed in more detail below. Furthermore, in other embodiments the row or rows of outlets can include a plurality of outlets that are longitudinally unaligned, such as being two or more offset rows of outlets.

In the exemplified embodiment, the applicator 150 comprises a concave dispensing surface 154 and the plurality of outlets 151 are located on the concave dispensing surface 154 of the applicator 150. More specifically, the concave dispensing surface 154 of the applicator 150 is formed by a depression 155 that is formed into the outer surface 126 of the handle 110. Furthermore, in the exemplified embodiment the concave dispensing surface 154 of the applicator 150 (and also the depression 155) is longitudinally elongated. More specifically, the depression 155 is in the shape of an elongated oval that is stretched or elongated longitudinally. Thus, the depression 155 starts at a first position $P_1$ on the handle 120 and extends longitudinally along the handle 120 to a second position $P_2$ on the handle 120, such that the first and second positions $P_1$, $P_2$ are longitudinally spaced apart from one another on the handle 120.

In the exemplified embodiment, the applicator 150 is positioned on the handle 120 so as to be closer to the proximal end 121 of the handle 120 than to the distal end 122 of the handle 120. However, the invention is not to be so limited in all embodiments and in certain other embodiments the applicator 150 can be positioned closer to the distal end 122 of the handle 120 than the proximal end 121 of the handle 120. Furthermore, in still other embodiments the applicator 150 may be located equi-spaced from both the proximal 121 and distal 122 ends of the handle 120. In still further embodiments, the applicator 120 may extend from the proximal end 121 of the handle 120 to the distal end 122 of the handle 120 such that the applicator 120 extends substantially the entire length of the handle 120. Thus, the applicator 150 can be located at any specific position on the handle 120 or on the body 105 of the oral care implement 100 and can extend for any desired length of the handle 120 or body 105 of the oral care implement 100.

The concave dispensing surface 154 of the applicator 150 can be conceptually longitudinally divided into a first region $R_1$, a second region $R_2$ and a third region $R_3$, the first region $R_1$ being located in between the second and third regions $R_2$, $R_3$. More specifically, in the exemplified embodiment the third region $R_3$ is located proximate the proximal end 121 of the handle 120, the first region $R_1$ is located adjacent the third region $R_3$ and the second region $R_2$ is located adjacent the first region $R_1$ and nearest to the distal end 122 of the handle 120. The first region $R_1$ has a first radius of curvature, the second region $R_2$ has a second radius of curvature and the third region $R_3$ has a third radius of curvature so that each of the second and third radiuses of curvature is greater than the first radius of curvature. Furthermore, in some embodiments the second and third radiuses of curvature can be the same. Thus, the shape of the depression 155, and more specifically of the concave dispensing surface 154 of the applicator 150, is similar to the shape of a user's teeth. Thus, the applicator 150 can be held up against a user's teeth and the shape of the applicator 150 will correspond to the shape of the user's teeth so that the oral care material 131 can be dispensed to a plurality of or all of the user's teeth simultaneously. This will be discussed in more detail below with reference to FIGS. 3-5.

In the exemplified embodiment, the applicator 150 further comprises a cushioning layer 156. The cushioning layer 156 is coupled to the outer surface 126 of the handle 120 along at least a portion of the depression 155. In the exemplified embodiment, the cushioning layer 156 overlays substantially the entirety of the depression 155 and of the concave dispensing surface 154 of the applicator 150. However, the invention is not to be so limited in all embodiments and in certain other embodiments the cushioning layer 156 may only cover the first region $R_1$ of the applicator 150, or the cushioning layer 156 may cover the entire first region $R_1$ and portions of the second and third regions $R_2$, $R_3$ of the applicator 150.

The cushioning layer 156 conforms to the shape of the concave dispensing surface 154 and may in certain embodiments be considered to comprise the concave dispensing surface 154 of the applicator 150. In certain embodiments, the cushioning layer 156 can be formed of a resilient material, such as for example without limitation elastomers including thermoplastic elastomers, unsaturated rubbers (i.e., natural polyisoprene, synthetic polyisoprene, polybutadiene, chloroprene rubber, butyl rubber, etc.) and saturated rubbers (ethylene propylene rubber, epichlorohydrin, polyacrylic rubber, silicone rubber, ethylene-vinyl acetate, etc.). In certain embodiments, thermoplastic elastomers are the preferred material for the cushioning layer 156. The cushioning layer 156 can be coupled to the outer surface 126 of the handle 120 in any desired fashion, such as by including mechanical interlocking features on the cushioning layer 156 and on the handle 120, by using adhesives or other fasteners, or the like. Although the exemplified embodiment of FIG. 2A illustrates such a cushioning layer 156, the invention is not to be so limited in all embodiments and in certain other embodiments the cushioning layer 156 may be omitted.

In certain embodiments, the cushioning layer 156 may be desired in order to achieve a desired level of comfort when using the applicator 150 to apply the oral care material 131 to a user's teeth or other oral surfaces. Specifically, as will be discussed in more detail below with reference to FIGS. 3-5, the applicator 150 is positioned into contact with or adjacent to a user's teeth. Thus, the cushioning layer 156 will provide a soft, cushioning layer in between the hard handle material and the user's teeth, gums or other oral surfaces to prevent injury to the user while using the applicator 150.

The oral care implement 100 further comprises an actuator 160. The actuator 160 is generically or schematically illustrated in FIG. 2A. The actuator 160 is operably coupled to the store of oral care material 131 to dispense the oral care material 131 through the plurality of outlets 151. Any technique for enabling the actuator 160 to dispense the oral care material 131 through the outlets 151 can be used. For example, in some embodiments the reservoir 130 or the store of oral care material 131 may be pressurized. Thus, upon actuating the actuator 160 (such as by pressing the actuator 160 in the direction of the arrow C), a one-way valve is opened and the oral care material 131 is forced out through the outlets 151. Such actuation/dispensing technique is similar to that of an aerosol spray. In other embodiments, the actuator 160 may operate in a similar manner to a spray bottle such that pressing the actuator 160 activates a pump that forces the oral care material 131 through the outlets 151. Of course, the above are merely examples of the manner of operation of the actuator 160 and any other technique for dispensing the oral care material 131 from the reservoir 130 through the outlets 151 to a user's teeth or other oral surfaces can be used.

The invention is not to be particularly limited by the manner in which the oral care material 131 is dispensed through the outlets 151 in all embodiments. However, in certain preferred embodiments the oral care material 131 is dispensed through the outlets 151 as a spray so that the oral care material 131 can be dispensed directly onto a user's teeth or other oral surfaces without additional actions required by the user to wipe or apply the oral care material 131 to the desired surface. Thus, in such embodiments actuation of the actuator 160 causes the oral care material 131 to be sprayed through one or more of the outlets 151 with sufficient force that the sprayed oral care material 131 is directly applied to the user's teeth or other oral surfaces.

In the exemplified embodiment, the applicator 150 is located on the front surface 123 of the handle 120 and the actuator 160 is located at and extends from the proximal end 121 of the handle 120. Of course, the invention is not to be so limited and the applicator 150 can be located on any portion of the outer surface 126 of the handle 120 or elsewhere on the body 105 or head 110. Furthermore, the actuator 160 can be located at any position along the body 105 of the oral care implement 100 as desired, such as being located on a thumb grip region of the handle 120, being located on the front or rear surface 123, 124 of the handle 120, being located on the head 110 or the like.

Figure 2B:
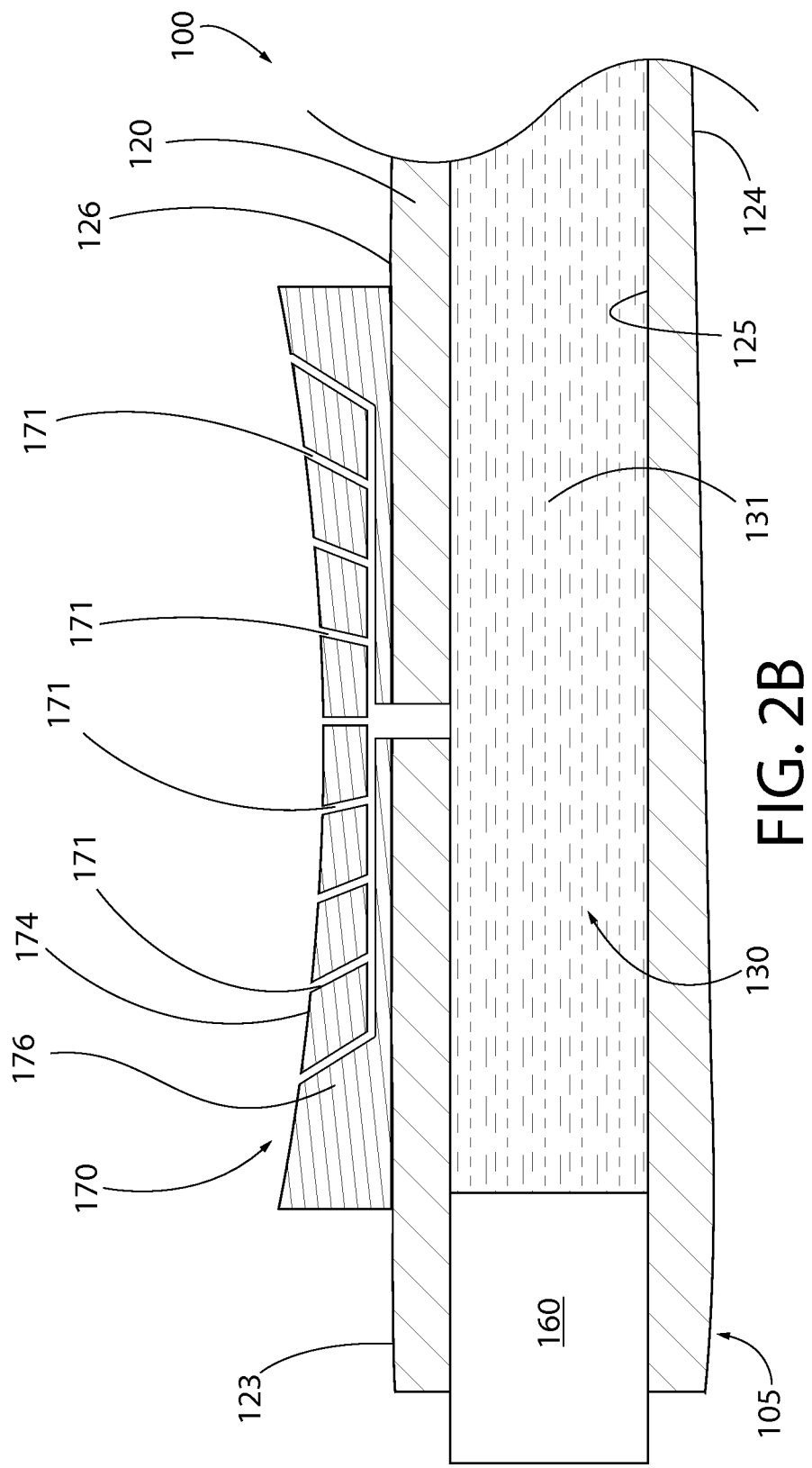
FIG. 2B is schematic cross-sectional view taken along line IIA-IIA of FIG. 1 in accordance with an alternative embodiment of the present invention.

Referring now to FIG. 2B, an alternative schematic representation of a cross-sectional view of the oral care implement 100 is provided. The embodiment of FIG. 2B is similar to the embodiment of FIG. 2A in many respects, and thus similar features will be similarly numbered. Specifically, in FIG. 2B the oral care implement 100 comprises a reservoir 130 that contains a store of oral care material 131 and an actuator 160 for dispensing the oral care material 131. In the embodiment of FIG. 2B, the handle 120 is cylindrically shaped and does not include a depression therein. The main difference between FIGS. 2A and 2B is the applicator, which will be discussed in more detail below.

The oral care implement 100 as depicted in FIG. 2B has an applicator 170. The applicator 170 comprises a plurality of outlets 171 that are in fluid communication with the store of oral care material 131 contained within the reservoir 130. Furthermore, the plurality of outlets 171 are located on a concave dispensing surface 174 of the applicator 170. However, in the embodiment of FIG. 2B the applicator 170 does not comprise a depression formed into the outer surface 126 of the handle 120. Rather, the applicator 170 comprises a base 176 and the plurality of outlets 171 are formed into the base 176. The base 176 of the applicator 170 is coupled to the outer surface 126 of the handle 120, and the base 176 of the applicator 170 comprises the concave dispensing surface 174 of the applicator 170.

In certain embodiments, the applicator 170, and more specifically the base 176 of the applicator 170, is formed of a resilient material, such as any of the materials discussed above including elastomers such as thermoplastic elastomers, saturated and unsaturated rubbers, and the like. In one preferred embodiment, the base 176 is formed of a thermoplastic elastomer. The base 176 of the applicator 170 can be coupled to the outer surface 126 of the handle 120 in any desired manner, such as by corresponding interlocking features on the outer surface 126 of the handle 120 and the base 176 of the applicator 170, adhesion, fasteners or the like. Furthermore, although the applicator 170 is illustrated and described herein as being coupled to the outer surface 126 of the handle 120, the invention is not to be so limited in all embodiments and in certain other embodiments the applicator 170 can be located on the head 110 of the oral care implement 100 or at any position on the body 105 as desired.

The specific locations and features of the applicator 150 and the outlets 151 discussed above with regard to FIG. 2A are applicable to the applicator 170 and the outlets 151. Thus, the base 176 of the applicator 170 is longitudinally elongated, and the outlets 151 are longitudinally spaced apart. Forming the applicator 170 so as to have the base 176 formed from a resilient material enhances the comfort to a user when the applicator 170 is being used to dispense the oral care material 131 to the user's oral surfaces. Furthermore, the applicator 170 may also be used as a hand grip for a user when the user is brushing his or her teeth. Thus, the concave dispensing surface 174 of the applicator 170 may have the dual purpose of conforming to the shape of a user's teeth during oral care material application/dispensing and conforming to a user's hand during brushing.

Figure 3:
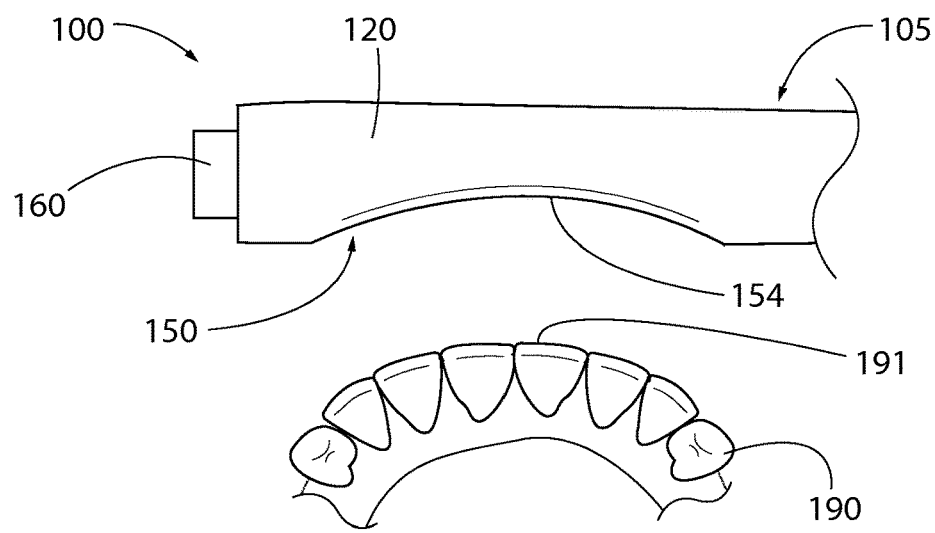
FIG. 3 is a schematic illustrating the oral care implement of FIG. 1 aligned with a user's teeth.
Figure 4:
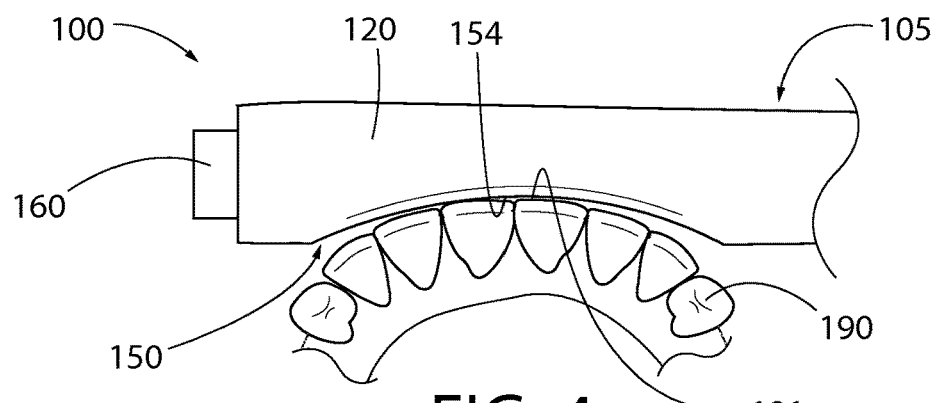
FIG. 4 is a schematic illustrating the oral care implement of FIG. 1 positioned adjacent to a user's teeth.
Figure 5:
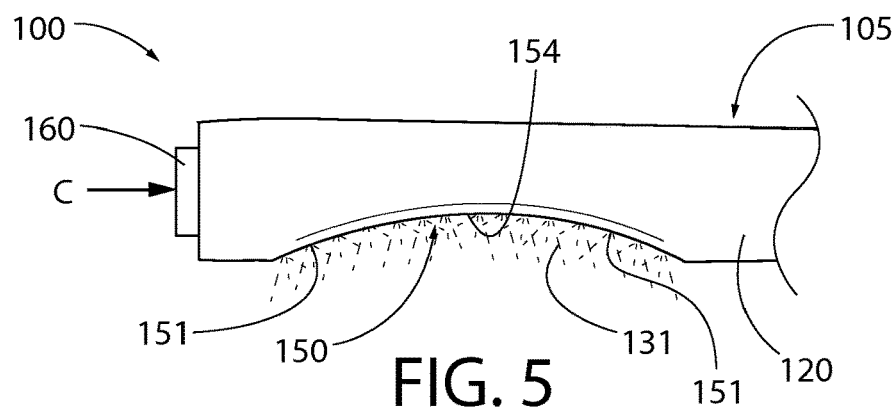
FIG. 5 is a schematic illustrating an actuator of the oral care implement of FIG. 1 being actuated to dispense an oral care material.

Referring to FIGS. 3-5 concurrently, use of the oral care implement 100 to dispense the oral care material 131 to a user's teeth 190 will be described. As discussed above, the oral care implement 100 has an applicator 150 with a concave dispensing surface 154. Similarly, the outer surface 191 of a set of human teeth, such as the user's teeth 190, is convex. In the exemplified embodiment, the concave dispensing surface 154 corresponds with the convex outer surface 191 of the user's teeth 190. Thus, as illustrated in FIG. 4, the oral care implement 100 can be held up to a user's teeth so that the concave dispensing surface 154 of the applicator 150 is adjacent to the outer surface 191 of the user's teeth 190. With the concave dispensing surface 154 of the applicator 150 positioned as depicted in FIG. 4, the actuator 160 can be actuated to dispense the oral care material 131 to the user's teeth.

As seen in FIG. 4, the concave dispensing surface 154 of the applicator 150 may only be long enough to align with a portion of the user's teeth, such as six of the user's teeth, eight of the user's teeth, or the like. However, in certain embodiments it may only be desirable or necessary to apply the oral care material 131 to the user's front-most teeth which are most commonly visible to other people. Thus, for example, when the oral care material 131 is a tooth whitening solution, it may only be desirable to apply the whitening solution to the user's front teeth (front six or eight teeth). The applicator 150 of the present invention will satisfy this desirability. Of course, in other embodiments where it may be desirable to apply the oral care material 131 to all of the user's teeth, the shape, length and arrangement of the applicator 150 can be modified as needed to achieve such dispensing.

Referring now to FIG. 5, the oral care implement 100 is illustrated with the actuator 160 being actuated so as to dispense the oral care material 131 from the applicator 150. In the exemplified embodiment, pressing the actuator 160 in the direction of the arrow C actuates the actuator 160 and causes the oral care material 131 to be dispensed from all of the outlets 151 of the plurality of outlets simultaneously. Thus, it can be appreciated that the applicator 150 can be used to apply the oral care material 131 directly to a plurality of a user's teeth (or all of the user's teeth in some embodiments) simultaneously with a single actuation of the actuator 160. Of course, the invention is not to be so limited in all embodiments and in certain other embodiments the applicator 150 may only dispense the oral care material 131 from one of the outlets or from some but not all of the outlets simultaneously as desired. The actuator 160 is biased into the non-dispensing position so that upon releasing the actuator 160 and no longer pressing the actuator 160 in the direction of the arrow C, the actuator 160 will bias back into the non-dispensing position. The actuator 160 may comprise a spring that biases the actuator 160 into the non-dispensing position or any other mechanical feature to bias the actuator 160 as discussed herein above.

In certain embodiments, a single depressing of the actuator 160 will cause a single spray of the oral care material 131 to be dispensed through the outlets 151. Specifically, in such embodiments a predetermined amount or dose of the oral care material 131 will be dispensed through the outlets 151 with each depressing/actuation of the actuator 160 regardless of the amount of time that the actuator 160 remains depressed/actuated. In still other embodiments, the oral care material 131 may continue to be dispensed through the outlets 131 for the entire time that the actuator 160 is being actuated. Thus, for example, if the actuator 160 is held into the depressed/actuated position for ten seconds, the oral care material 131 will dispense through the outlets 131 for the entire ten seconds.

Figure 6:
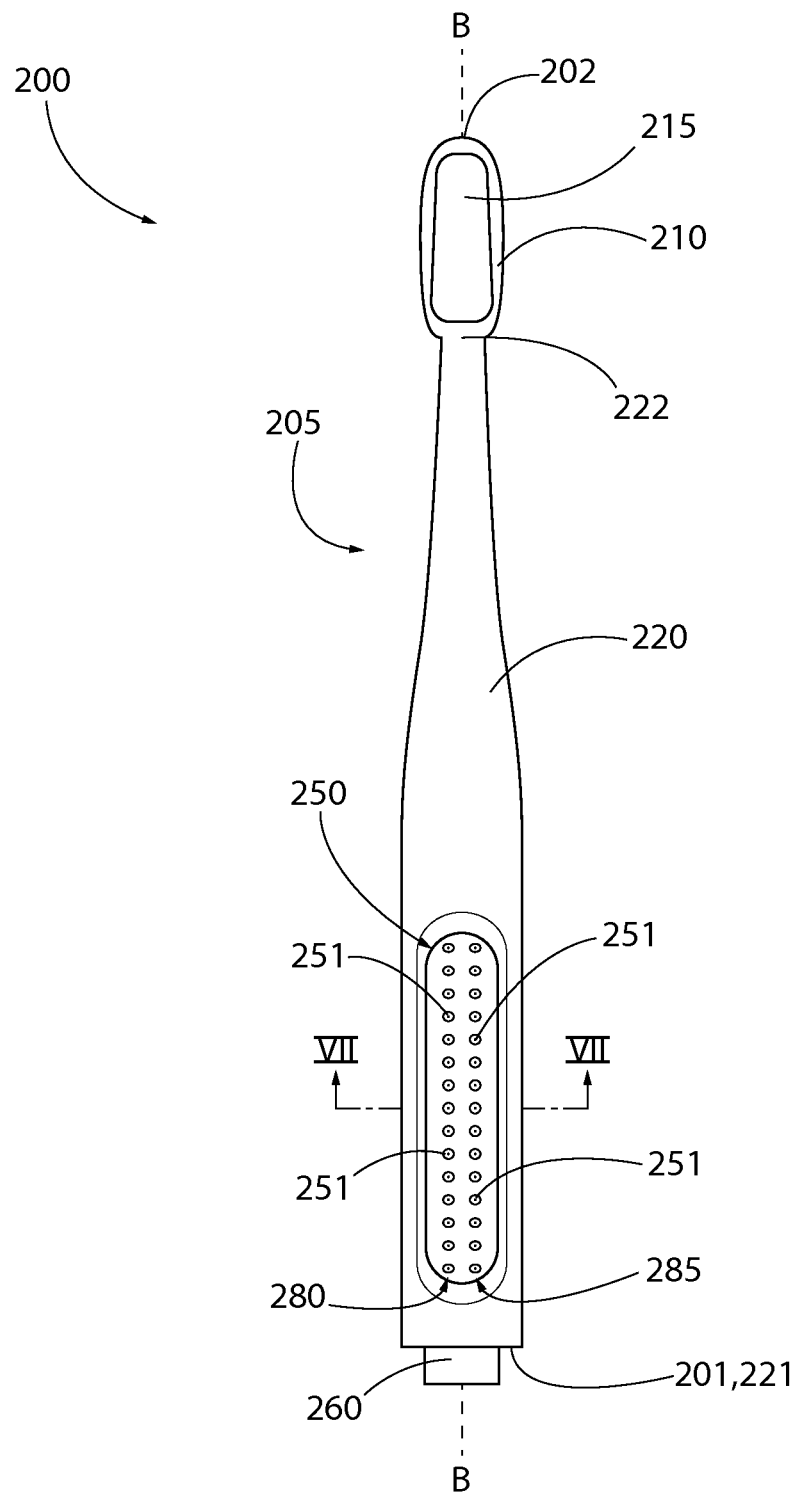
FIG. 6 is a front view of an oral care implement in accordance with a second embodiment of the present invention.
Figure 7:
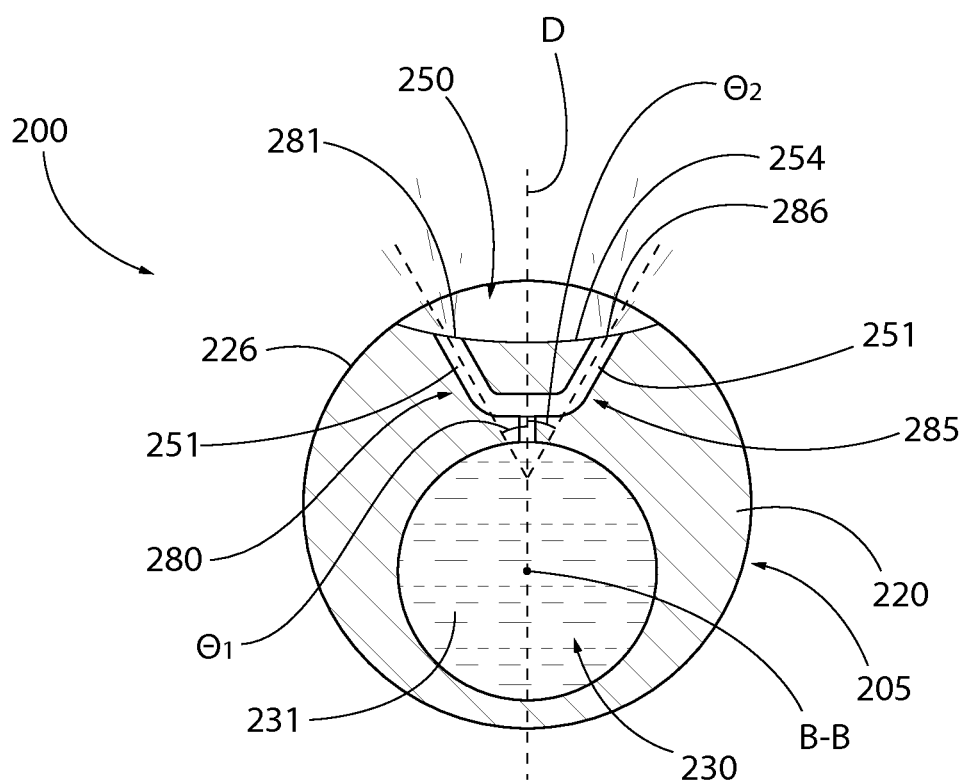
FIG. 7 is a schematic cross-sectional view taken along line VII-VII of FIG. 6.

Referring now to FIGS. 6 and 7 concurrently, an oral care implement 200 is illustrated in accordance with an alternative embodiment of the present invention. The oral care implement 200 is similar to the oral care implement 100 in many respects, and thus similar features will be similarly numbered except that the 200-series of numbers will be used. Certain features of the oral care implement 200 may be similarly numbered as the oral care implement 100 but might not be described in detail herein in the interest of brevity, it being understood that the discussion of the similar component on the oral care implement 100 applies. Furthermore, features of the oral care implement 100 described above that are not illustrated on the oral care implement 200 are applicable to the oral care implement 200 in certain embodiments and vice versa. Thus, various combinations of the description below with regard to the oral care implement 200 and the description above with regard to the oral care implement 100 are within the scope of the present invention in some embodiments.

The oral care implement 200 comprises a body 205 that extends along a longitudinal axis B-B from a proximal end 201 to a distal end 202. The body 205 of the oral care implement 200 generally comprises a handle 220 extending from a proximal end 221 (which is the same as the proximal end 201 of the body 205) to a distal end 222 and a head 210 operably coupled to the distal end 222 of the handle 220. The head 220 comprises a plurality of tooth cleaning elements 215 extending therefrom to clean a user's teeth and other oral surfaces. The handle 220 is sized and configured to enable a user to manipulate the oral care implement 100 during tooth brushing. The general structural features and materials described above with regard to the oral care implement 100 are applicable to the oral care implement 200 except as discussed below.

The oral care implement 200 comprises an applicator 250 comprising a plurality of outlets 251 that are in fluid communication with a store of oral care material 231. As discussed above with regard to the oral care implement 100, the store of oral care material 230 may in some embodiments be located within a reservoir 230 in the handle 220 of the oral care implement 200, although it can be located at other positions within the body 205 in other embodiments.

The plurality of outlets 251 of the applicator 250 are located on a concave dispensing surface 254 of the applicator 150. The details of the different embodiments of the concave dispensing surface 254 have been discussed in detail above with specific reference to FIGS. 2A and 2B. In the embodiment of FIGS. 6 and 7, the plurality of outlets 251 comprise a first row of outlets 280 and a second row of outlets 285. The plurality of outlets 251 of the first row of outlets 280 are arranged in a single longitudinally aligned row in a longitudinally spaced-apart manner. Similarly, the plurality of outlets 251 of the second row of outlets 285 are arranged in a single longitudinally aligned row in a longitudinally spaced-apart manner. The first row of outlets 280 and the second row of outlets 285 are transversely spaced apart from one another. In the exemplified embodiment, the outlets 251 of the first row of outlets 280 are transversely aligned with the outlets 251 of the second row of outlets 285, although in other embodiments the outlets 251 of the first and second rows of outlets 280, 285 may be transversely offset.

For reference, a reference plane D is illustrated in FIG. 7 that is coextensive and aligned with the longitudinal axis B-B and that crosses through the space between the first and second rows of outlets 280, 285. The outlets 251 of the first row of outlets 280 are oriented at a first angle $\Theta_1$ relative to the reference plane D and the outlets 251 of the second row of outlets 285 are oriented at a second angle $\Theta_2$ relative to the reference plane D. In the exemplified embodiment, each of the first and second angles $\Theta_1$, $\Theta_2$ are substantially the same, such as being between 15° and 45°, more specifically between 20° and 40°, still more specifically between 25° and 35°, and even more specifically approximately 30°. However, angles outside of the noted ranges are also possible in other embodiments as desired.

The outlets 251 of the first row of outlets 280 terminate at openings 281 in the outer surface 226 of the handle 220. The outlets 251 of the second row of outlets 285 terminate at openings 286 in the outer surface 226 of the handle 220. In the exemplified embodiment, the openings 281 of the outlets 251 of the first row of outlets 280 and the openings 286 of the outlets 251 of the second row of outlets 285 are located on opposite sides of the reference plane D. Thus, due to the angle of orientation of the outlets 251 of the first and second rows 280, 285 and due to the positioning of the openings 281, 286 on opposite sides of the reference plane D, the outlets 251 of the first row of outlets 280 can be used to dispense the oral care material 231 to a user's upper teeth while the outlets 251 of the second row of outlets 285 can be used to simultaneously dispense the oral care material 231 to the user's lower teeth. Thus, using the oral care implement 200, the applicator 250 can be positioned near or adjacent to a user's teeth, and then the actuator 260 can be actuated. Actuation of the actuator will cause the oral care material 231 to be dispensed through each of the outlets 251 of the first and second rows of outlets 280, 285 simultaneously to thereby simultaneously dispense the oral care material 231 to the user's upper and lower (or top and bottom) teeth.

In the exemplified embodiments, there are fifteen outlets illustrated in each row of the outlets (both in the oral care implement 100 and in the oral care implement 200). However, the invention is not to be so limited in all embodiments and more or less than fifteen outlets can be used in other embodiments. The illustration of fifteen outlets is simply one representative example that is not intended to limit the invention.

As noted above, various combinations of the features described above with regard to the embodiment of the oral care implement 100 and the oral care implement 200 are possible. Thus, the oral care implement 200 may include a cushioning layer, or the applicator 250 may be formed with a base that is coupled to the outer surface 226 of the handle 220. In other words, although certain components are only described herein with regard to the oral care implement 100, they are equally applicable to the oral care implement 200.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
    a body comprising a handle and a head coupled to a distal end of the handle, the body extending along a longitudinal axis;
    at least one tooth cleaning element located on the head;
    a store of oral care material located within the body;
    an applicator on the handle, the applicator comprising a plurality of outlets in fluid communication with the store of oral care material, the plurality of outlets located on a concave dispensing surface of the applicator; and
    an actuator operably coupled to the store of oral care material to dispense the oral care material through the plurality of outlets.

2. The oral care implement according to claim 1 wherein the applicator comprises a base and the plurality of outlets are formed into the base, and wherein the base of the applicator is coupled to an outer surface of the handle, wherein the body is formed of a rigid plastic material and the base of the applicator is formed of a resilient material.

3. The oral care implement according to claim 1 wherein the applicator comprises a depression formed into an outer surface of the handle, the depression being longitudinally elongated, wherein the applicator further comprises a cushioning layer coupled to the outer surface of the handle along at least a portion of the depression, the cushioning layer formed of a thermoplastic elastomer.

4. The oral care implement according to claim 1 wherein the plurality of outlets are arranged in a single row in a longitudinally spaced-apart manner.

5. The oral care implement according to claim 1 wherein the plurality of outlets comprise a first row of outlets and a second row of outlets, wherein outlets of the first row of outlets are oriented to dispense the oral care material to a user's upper teeth while outlets of the second row of outlets are oriented to simultaneously dispense the oral care material to the user's lower teeth.

6. The oral care implement according to claim 5 wherein the outlets of the first row of outlets are oriented at a first angle relative to a reference plane that is coextensive with the longitudinal axis of the body and the outlets of the second row of outlets are oriented at a second angle relative to the reference plane, the first and second angles being substantially the same, and the outlets of the first row of outlets and the outlets of the second row of outlets having openings located on opposite sides of the reference plane.

7. The oral care implement according to claim 1 wherein actuation of the actuator dispenses the oral care material through each of the plurality of outlets simultaneously.

8. An oral care implement comprising:
a body comprising a handle and a head coupled to a distal end of the handle, the body extending along a longitudinal axis;
a plurality of tooth cleaning elements extending from the head;
a store of oral care material located within the body;
an applicator on the body, the applicator comprising a plurality of outlets in fluid communication with the store of oral care material, the plurality of outlets positioned on the handle in a longitudinally spaced-apart manner; and
an actuator operably coupled to the store of oral care material to dispense the oral care material through the plurality of outlets.

9. The oral care implement according to claim 8 wherein the plurality of outlets are arranged on the handle in a single row.

10. The oral care implement according to claim 8 wherein the plurality of outlets comprise a first row of outlets and a second row of outlets, wherein outlets of the first row of outlets are oriented to dispense the oral care material to a user's upper teeth while outlets of the second row of outlets are oriented to simultaneously dispense the oral care material to the user's lower teeth.

11. The oral care implement according to claim 10 wherein the outlets of the first row of outlets are oriented at a first angle relative to a reference plane that is coextensive with the longitudinal axis of the body and the outlets of the second row of outlets are oriented at a second angle relative to the reference plane, the first and second angles being substantially the same, and the outlets of the first row of outlets and the outlets of the second row of outlets having openings located on opposite sides of the reference plane.

12. The oral care implement according to claim 8 wherein the applicator comprises a base and the plurality of outlets are formed into a concave dispensing surface of the base, and wherein the base of the applicator is coupled to an outer surface of the handle.

13. The oral care implement according to claim 12 wherein the handle is formed of a rigid plastic material and the base of the applicator is formed of a resilient material.

14. The oral care implement according to claim 8 wherein the applicator comprises a depression formed into an outer surface of the handle, the depression forming a concave dispensing surface and being longitudinally elongated, the plurality of outlets located on the concave dispensing surface.

15. The oral care implement according to claim 14 wherein the applicator further comprises a cushioning layer coupled to the outer surface of the handle along at least a portion of the depression, the cushioning layer formed of a thermoplastic elastomer.

16. The oral care implement according to claim 8 wherein actuation of the actuator dispenses the oral care material through each of the plurality of outlets simultaneously.

17. The oral care implement according to claim 8 further comprising a reservoir located within the handle, the reservoir containing the store of oral care material.

18. The oral care implement according to claim 17 wherein the applicator is located on the handle and wherein the actuator is located at a proximal end of the handle.

19. A toothbrush comprising:
a handle extending along a longitudinal axis;
a head coupled to a distal end of the handle, the head having a front surface, the front surface of the head having one or more tooth cleaning elements extending therefrom;
a store of oral care material located within a body;
an applicator on the handle, the applicator comprising a plurality of outlets in fluid communication with the store of oral care material, the plurality of outlets located on a concave dispensing surface of the applicator; and
an actuator operably coupled to the store of oral care material to dispense the oral care material through the plurality of outlets;
wherein the applicator is longitudinally elongated in the direction of the longitudinal axis.

20. The toothbrush of claim 19 wherein the toothbrush has a front surface and further comprising at least one tooth cleaning element located on the head, wherein the at least one tooth cleaning element extends from the front surface of the toothbrush and the applicator is located on the front surface of the toothbrush.

* * * * *